United States Patent [19]

Morledge

[11] 4,223,669

[45] Sep. 23, 1980

[54] SURGICAL DRAPE SUPPORT APPARATUS

[76] Inventor: Thomas E. Morledge, 208 Mountain View Blvd., Billings, Mont. 59101

[21] Appl. No.: 954,940

[22] Filed: Oct. 26, 1978

[51] Int. Cl.³ .............................................. A61B 19/00
[52] U.S. Cl. ........................... 128/132 D; 128/204.18; 128/205.26; 128/910; 128/139
[58] Field of Search ............... 128/132 D, 132 R, 139, 128/147, 140 R, 185, 188, 195, 205, 187, 203, 204, 1 B, 191 A, 298, 299, 204.18, 205.26; 98/115 HL, 36

[56] References Cited

U.S. PATENT DOCUMENTS

| 2,290,437 | 7/1942 | Kilgore et al. | 128/132 D X |
| 3,859,993 | 1/1975 | Bitner | 128/185 X |
| 3,881,477 | 5/1975 | Von Otto | 128/132 D |
| 3,999,541 | 12/1976 | Tabor | 128/191 A |

FOREIGN PATENT DOCUMENTS 107372  5/1939  Australia ............................. 128/191 A Primary Examiner—Henry J. Recla
Attorney, Agent, or Firm—Arthur L. Urban

[57] ABSTRACT

Surgical drape support apparatus including a generally U-shaped horizontal base frame having a longitudinal section, transverse sections extending from the longitudinal section adjacent to the ends thereof substantially perpendicular to the longitudinal section, a support section extending generally vertically from the longitudinal section adjacent one of the transverse sections, an upper section extending from the support section adjacent the free end thereof, the upper section extending generally horizontally from the support section substantially parallelt to and above the transverse section closest thereto, the upper section and the support section having passages therethrough and the upper section and the suport section having a plurality of spaced openings along at least a portion of their lengths with the openings being oriented toward the area circumscribed by the base frame.

8 Claims, 3 Drawing Figures

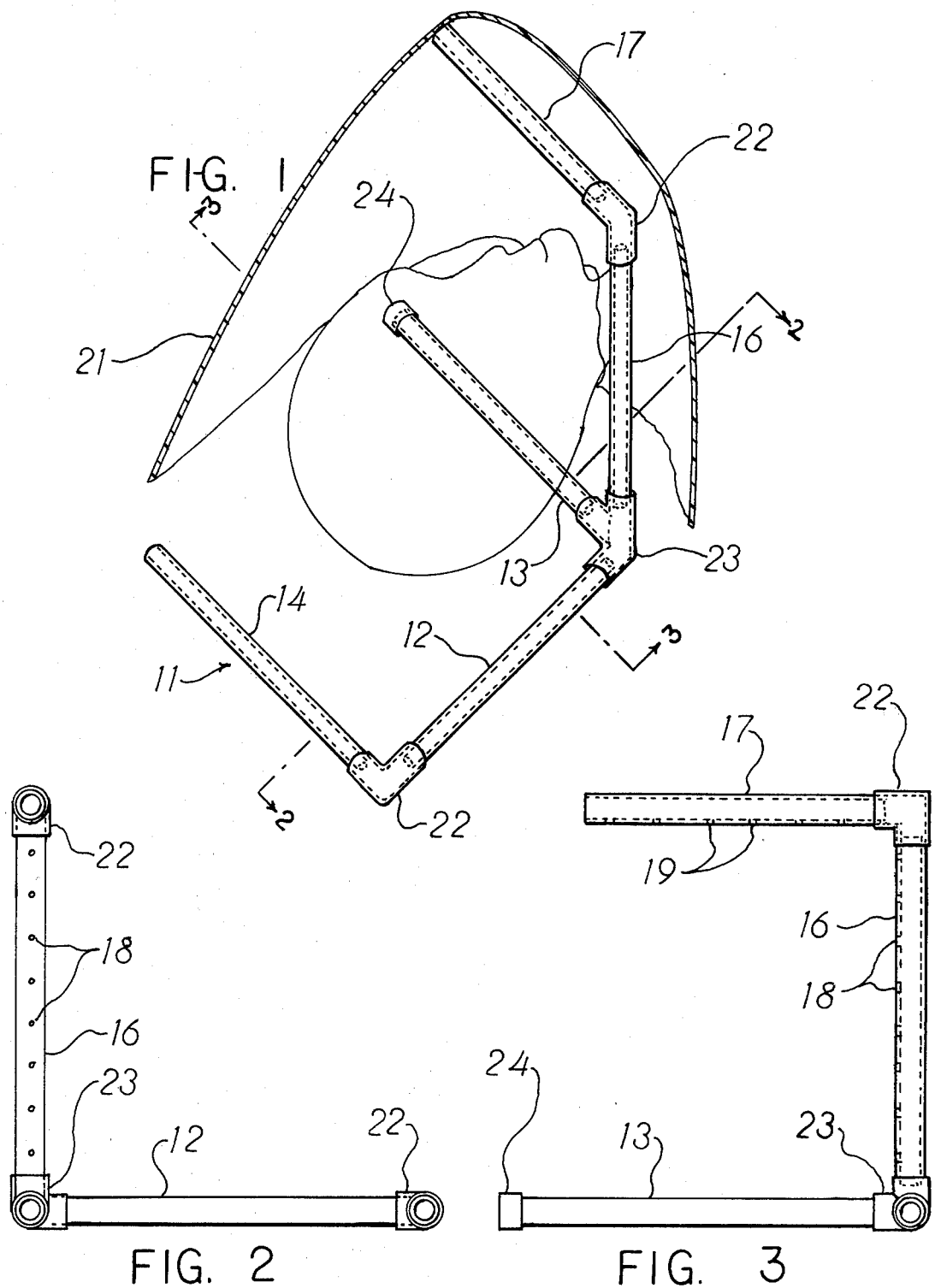

SURGICAL DRAPE SUPPORT APPARATUS

This invention relates to a novel apparatus for supporting a surgical drape and more particularly relates to a new apparatus for supporting a drape during surgery.

Drapes sometimes are used during surgery to cover the area surrounding that portion of the body undergoing surgery. This is done to reduce the possibility of contamination to the area in which surgery is being performed from the adjacent area. For example, a plastic sheet may be used with an opening at the area of the surgery. The edges of the opening may be taped to the patient's body to hold it tightly in place.

The use of such surgical drapes ordinarily does not present any problems. However, with surgery on portions of the head, drapes may create difficulties. If the surgery is done under local anesthesia, it is essential that the patient be able to breath properly. For example, certain eye surgery such as the removal of cataracts may be performed under local anesthesia. With such surgery, a surgical drape covers the head of the patient with an opening for the eye.

The closeness of the drape around the face and particularly the nose and mouth often cause the patient to suffer anxiety. In addition, in some cases such as when the drape is a plastic sheet, the patient may experience anoxia due to restriction of his air supply. The anxiety and/or anoxia can create serious problems during surgery. Thus, the surgeon is faced with the choice of using a surgical drape at the expense of the patient's general comfort and condition or of not using a surgical drape at the risk of contaminating the area of surgery. Neither choice fulfills the surgeon's needs.

The present invention provides a novel surgical drape support apparatus which significantly reduces a patient's discomfort. Also, the drape support of the invention reduces a patient's anxieties. Furthermore, the surgical drape support facilitates normal breathing by the patient. In addition, the drape support substantially eliminates the possibility of anoxia occurring.

The drape support of the present invention is simple in design and convenient to use. Moreover, the drape support can be modified easily to meet special patient requirements. Also, the surgical drape support of the invention can be fabricated from commercially available materials without special skills or tools.

Other benefits and advantages of the novel surgical drape support of the invention will be apparent from the following description and the accompanying drawings in which:

FIG. 1 is a view in perspective of one form of the surgical drape support apparatus of the invention;

FIG. 2 is a view partially in section of the surgical drape support apparatus shown in FIG. 1 taken along line 2—2; and FIG. 3 is a view partially in section of the surgical drape support apparatus shown in FIG. 1 taken along line 3—3.

As shown in the drawings, one form of the novel surgical drape support apparatus of the present invention includes a generally U-shaped horizontal base frame 11 having a longitudinal section 12 and transverse sections 13 and 14. Transverse sections 13 and 14 extend from longitudinal section 12 adjacent the ends thereof. The transverse sections 13 and 14 extend from longitudinal section 12 substantially perpendicular thereto.

A support section 16 extends upwardly from longitudinal section 12 adjacent one of the transverse sections 13 or 14. Support section 16 extends upwardly from longitudinal section 12 in a generally vertical direction. Advantageously, as shown in the drawings, support section 16 extends upwardly from the juncture of longitudinal section 12 with one of the transverse sections.

An upper section 17 extends from support section 16 adjacent the free end at the top thereof. Upper section 17 extends generally horizontally from support section 16. Upper section 17 also is disposed substantially parallel to and above one of the transverse sections 13 or 14. Preferably, upper section 17 is disposed directly above one of the transverse sections.

Support section 16 and upper section 17 have passages therethrough. Support section 16 and upper section 17 also have a plurality of spaced openings 18 and 19, respectively, along at least a portion of their lengths. Openings 18 and 19 communicate with the passages through the support section 16 and the upper section 17. Openings 18 and 19 are oriented toward the area circumscribed by the base frame 11. As shown, the openings 18 in support section 16 advantageously are disposed in a generally linear arrangement along the side of the section facing toward transverse section 13. Similarly, the openings 19 in upper section 17 preferably are disposed in a generally linear configuration along the bottom of the section.

The surgical drape support apparatus of the present invention may be fabricated from a variety of materials such as metals, plastics and the like. Advantageously, at least a portion of the apparatus may be formed of a continuously length of tubing with the side portions affixed thereto. Preferably, the apparatus is fabricated of plastic tubing interconnected by connectors such as shown in the drawings as elbows 22 and 90° tee 23. If desired, one or more of the open tubing ends may be sealed with caps 24.

The surgical drape support apparatus of the invention is used by placing the transverse sections 13 and 14 of the base frame 11 transversely of the operating table and the longitudinal section 12 parallel to one side of the operating table. A suitable head support (not shown) is positioned within the area circumscribed by the base frame. The patient's head next is positioned on the head support with transverse section under his neck and section 14 above his head. Longitudinal section 12 is disposed along one side of his head.

To provide a proper fit for a particular patient's head, support section 16 advantageously is separable from the base frame 11 and support section 16 and upper section 17 are of different lengths. With this construction, the support section and the upper section can be interchanged to raise or lower the height of the apparatus from the patient's face.

The apparatus is connected to a source of air (not shown). Advantageously, the apparatus is connected to a vacuum line. This attachment permits air to move through the passages in the support section 16 and upper section 17. The air is either drawn through or forced from the openings 18 and 19 in the respective sections. In the structure shown in the drawings, the sections of the base frame 11 also have passages therethrough. This enables an air or vacuum line to be connected to one of the transverse sections (14) and cap placed over the end of transverse section 13.

The patient is prepared for surgery with the drape 21 placed over his head and the apparatus of the invention.

The drape is kept away from his face since it is suspended on the upper section 17 of the apparatus. An opening (not shown) in the drape makes the area undergoing surgery accessible to the surgeon. The edges of the opening are secured tightly to the patient's head. The flow of air through the passages of the apparatus is adjusted to circulate air past the patient's head. In the preferred condition in which the apparatus is connected to a vacuum line, air is drawn under the edges of the drape 21 and through the openings 18 and 19 of the support section 16 and the upper section 17. The air moves through sections 12 and 14 and is drawn into the vacuum line. In this way, a flow of air is provided for the patient so he can breath normally during surgery under local anesthesia.

The above description and the accompanying drawings show that the present invention provides a novel surgical drape support apparatus which significantly reduces a patient's discomfort and anxieties during surgery. Furthermore, the surgical drape support of the invention allows a patient to breath normally during surgery so that the possibility of anoxia is substantially eliminated.

Moreover, the drape support apparatus of the present invention is simple in design and convenient to use. In addition, the drape support can be modified easily to meet special patient requirements and needs. Also, the surgical drape support apparatus of the invention can be fabricated from commercially available materials relatively inexpensively without special tools or skills.

It will be apparent that various modifications can be made in the particular surgical drape support apparatus shown in the drawings and described above within the scope of the invention. For example, the size and configuration of the components of the apparatus can be changed to meet specific requirements. Also, the interconnection of the sections to provide passages for the movement of air can be different so long as the functioning of the apparatus is not deleteriously affected. Therefore, the scope of the invention is to be limited only by the following claims.

What is claimed is:

1. Surgical drape support appartus including a horizontal base frame having a longitudinal section, transverse sections extending from said longitudinal section adjacent the ends thereof, said transverse sections being disposed substantially perpendicular to said longitudinal section, a support section extending generally vertically from said longitudinal section adjacent one of said transverse sections, an upper section extending from said support section adjacent the free end thereof, said upper section extending generally horizontally from said support section substantially parallel to and above said transverse section closest thereto, said upper section and said support section having passages therethrough and a plurality of spaced openings along at least a portion of their lengths communicating with said passages, said openings being oriented toward the area circumscribed by and projected upwardly from said base frame, said apparatus including means for adapting said passages to a source of positive or negative air pressure.

2. Surgical drape support apparatus according to claim 1 wherein said support section is separable from said base frame.

3. Surgical drape support apparatus according to claim 1 wherein the sections of said base frame are affixed to each other to form a unitary structure.

4. Surgical drape support apparatus according to claim 1 wherein said upper section and said support section are of different lengths.

5. Surgical drape support apparatus according to claim 1 wherein said upper section is disposed directly above one of said transverse sections.

6. Surgical drape support apparatus according to claim 1 wherein all of the sections of said apparatus are lengths of hollow tubing.

7. Surgical drape support apparatus according to claim 1 wherein said apparatus is formed of plastic.

8. Surgical drape support apparatus according to claim 1 wherein said longitudinal section and at least one of said transverse sections have passages connected to the passages of said upper section and said support section for the movement of air therethrough.

* * * * *